US00PP25508P2

(12) United States Plant Patent
Ault

(10) Patent No.: US PP25,508 P2
(45) Date of Patent: May 5, 2015

(54) ***BAPTISIA* PLANT NAMED 'ROYAL PURPLE'**

(50) Latin Name: ***Baptisia* hybrid**
Varietal Denomination: Royal Purple

(71) Applicant: James Robert Ault, Libertyville, IL (US)

(72) Inventor: James Robert Ault, Libertyville, IL (US)

(73) Assignee: Chicago Land Grows, Inc, Glencoe, IL (US)

( * ) Notice: Subject to any disclaimer, the term of this patent is extended or adjusted under 35 U.S.C. 154(b) by 167 days.

(21) Appl. No.: 13/987,050

(22) Filed: Jun. 28, 2013

(51) Int. Cl.
*A01H 5/02* (2006.01)

(52) U.S. Cl.
USPC ..... Plt./263.1

(58) Field of Classification Search
CPC ..... A01H 5/02
USPC ..... Plt./263.1, 226
See application file for complete search history.

*Primary Examiner* — June Hwu
(74) *Attorney, Agent, or Firm* — Penny J. Aguirre

(57) ABSTRACT

A new cultivar of *Baptisia*, 'Royal Purple' that is characterized by its racemes of flowers that are deep violet-blue in color, its dense vase-shaped plant habit when young and a dense broadly rounded plant habit and slightly smaller in size when mature, stipules at the base of the peduncle that are small in size, its inflorescences in which about 75% arises above the foliage and its ability to be readily propagated using stem shoot tip cuttings.

2 Drawing Sheets

Botanical classification: *Baptisia* hybrid.
Cultivar designation: 'Royal Purple'.

BACKGROUND OF THE INVENTION

The present invention relates to a new and distinct cultivar of hybrid *Baptisia* plant, botanically known as *Baptisia* 'Royal Purple' and will be referred to hereafter by its cultivar name, 'Royal Purple'. The new cultivar represents a new false indigo, an herbaceous perennial grown for landscape use.

The new invention arose from an ongoing breeding program in a dedicated test plot in Glencoe, Ill. The objective of the breeding program is to develop novel interspecific hybrids of *Baptisia* that exhibit unique flower coloration, hybrid vigor, ease of clonal propagation, and desirable plant habits.

'Royal Purple' was selected as a single unique plant by the Inventor in 2009 after evaluating seedlings that derived from a cross made in 2004 between unnamed plants of hybrid *Baptisia* from the Inventor's breeding program. The female parent was a seedling that derived from open pollination of an interspecific hybrid *Baptisia* (*australis*×*leucophaea*). The male parent was a seedling that derived from open pollination of an interspecific hybrid *Baptisia* (*australis*×*sphaerocarpa*).

Asexual propagation of the new cultivar was first accomplished by stem shoot tip cuttings in July of 2009 in Glencoe, Ill. under the direction of the Inventor. Asexual propagation by stem shoot tip cuttings has determined that the characteristics of the new cultivar are stable and are reproduced true to type in successive generations.

SUMMARY OF THE INVENTION

The following traits have been repeatedly observed and represent the characteristics of the new cultivar as observed in Glencoe, Ill. These attributes in combination distinguish 'Royal Purple' as a unique cultivar of *Baptisia*.

1. 'Royal Purple' produces racemes of flowers that are deep violet-blue in color (deeper violet-blue than other cultivars known to the Inventor).
2. 'Royal Purple' exhibits a dense vase-shaped plant habit when young and a dense broadly rounded plant habit and slightly smaller in size when mature.
3. 'Royal Purple' produces stipules at the base of the peduncle that are small in size.
4. 'Royal Purple' exhibits inflorescences in which about 75% arises above the foliage at anthesis.
5. 'Royal Purple' is readily propagated from stem shoot tip cuttings.

The female parent of 'Royal Purple' differs from 'Royal Purple' in having a distinctly backswept banner that almost touches, whereas 'Royal Purple' has banners that are flat or only slightly backswept and do not touch. The female parent also differs from 'Royal Purple' in having inflorescences that are longer with 25% emerging above the foliage at anthesis (more hidden in the foliage). The male parent differs from 'Royal Purple' in having smaller flowers that are burgundy in color. 'Royal Purple' can be most closely compared to typical plants of *Baptisia australis* and to the cultivar 'Twilite' (U.S. Plant Pat. No. 19,011). *Baptisia australis* is similar to 'Royal Purple' in plant habit (vase-shaped when young and broadly rounded when mature) and in season of bloom. *Baptisia australis* differs from 'Royal Purple' in having flowers that are bluer in color, in having stipules at the base of the peduncle that are larger in size (2.5 cm), and in having longer inflorescences. 'Twilite' is similar to 'Royal Purple' in blooming period and in having a dense plant habit that is vase-shaped when young and broadly rounded when mature. 'Twilite' differs from 'Royal Purple' in having flowers that are bi-colored (violet purple with a yellow keel), in having inflorescences with 25% emerging above the foliage at anthesis (more hidden in the foliage), and in having a taller plant height.

BRIEF DESCRIPTION OF THE DRAWINGS

The accompanying colored photographs illustrate the overall appearance and distinct characteristics of the new *Bapti-*

*sia*. The photographs were taken of plants five years in age as grown outdoors in a trial plot in Glencoe, Ill.

Figure 1:
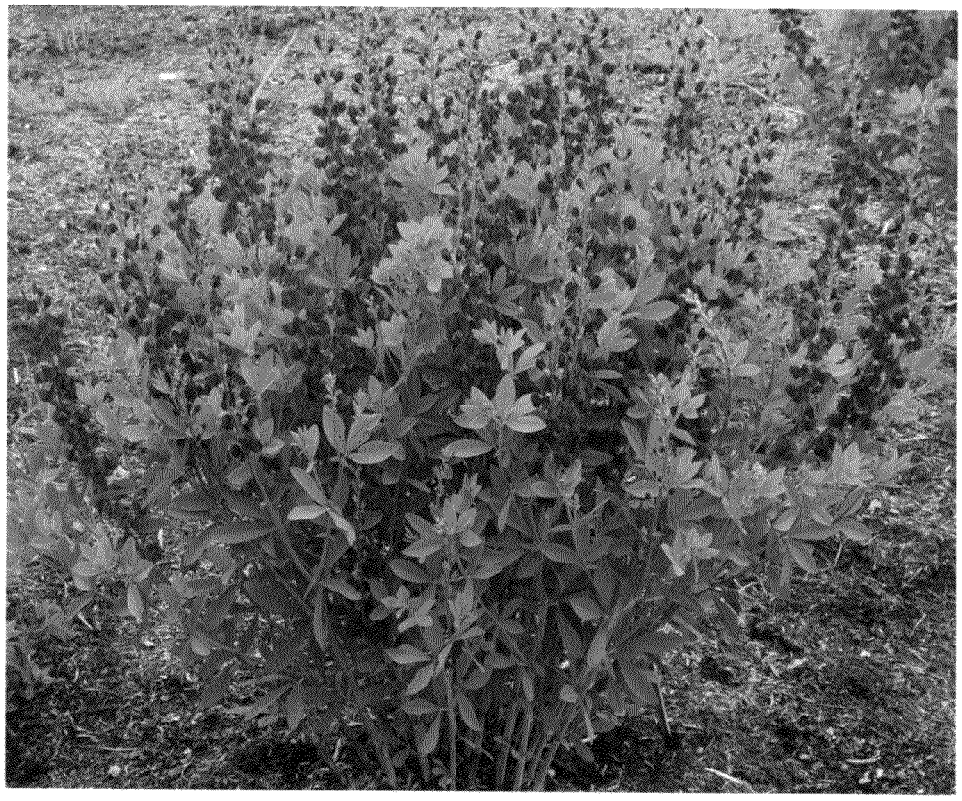

The photograph in FIG. 1 is a side view of 'Royal Purple' in bloom and illustrates the plant habit and flowering habit.

Figure 2:
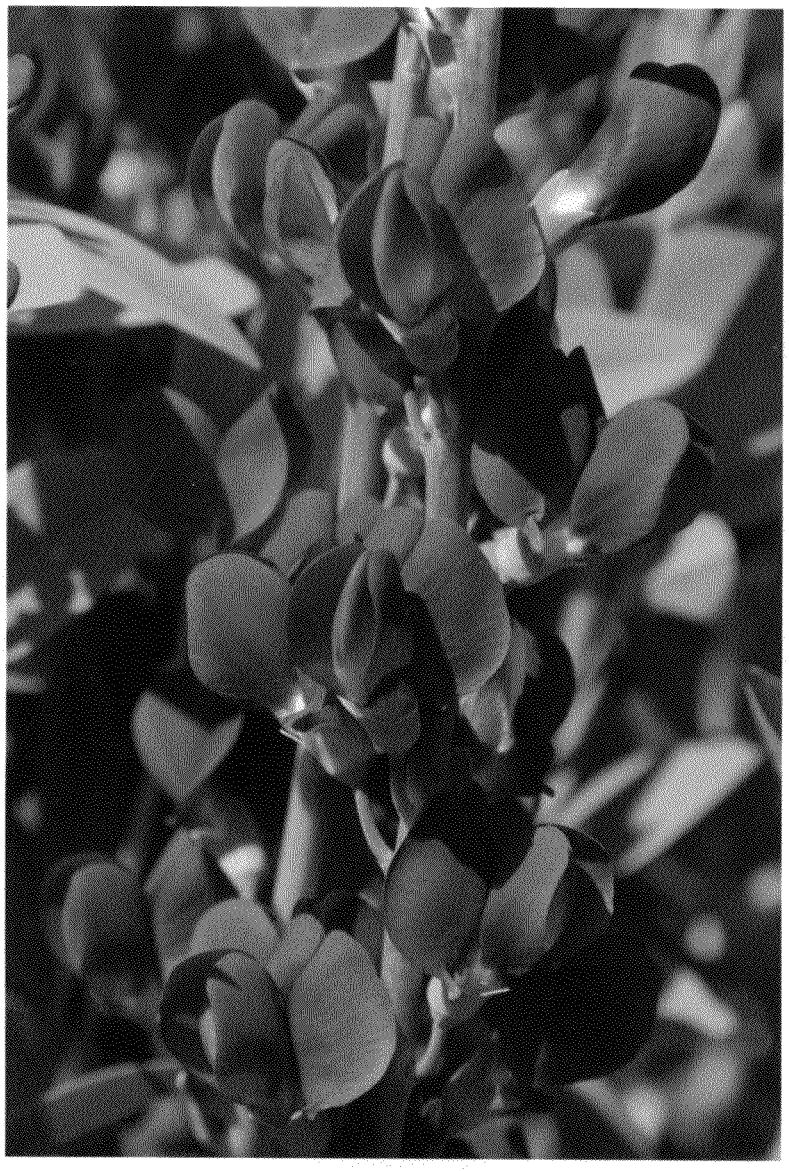

The photograph in FIG. 2 provides a close up view of the flowers of 'Royal Purple'.

The colors in the photographs are as close as possible with the photographic and printing technology utilized and the color values cited in the detailed botanical description accurately describe the colors of the new *Baptisia*.

DETAILED BOTANICAL DESCRIPTION OF THE PLANT

The following is a detailed description of 7 year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—About 3 weeks commencing in mid to late May in Glencoe, Ill.

*Plant habit*.—Upright when young and broadly rounded when mature.

*Height and spread*.—Reaches an average of 1.1 m in width and 1.34 m in height at 7 years in age and 1.05 m in height and 1.72 cm in width at 9 years in age.

*Hardiness*.—At least in U.S.D.A. Zones 4 to 7.

*Diseases and pests*.—No discernable disease or pest problems have been observed.

*Root description*.—Deep rooted, fibrous.

*Propagation*.—Stem shoot tip cuttings (readily propagated).

*Growth rate*.—Vigorous.

Stem description:

*Branch habit*.—Densely branched; average of 96 branches with an average of 3 secondary branches, and 2 tertiary branches on a 7 year-old plant with an average of 131 main stems on a 9 year-old plant.

*Stem size*.—Main stem; an average of 105 cm (including peduncle) in length and 5.2 mm in width (10 mm at base), secondary; average of 50 cm in length and 3.5 mm, tertiary; an average of 15 cm in length and 1.8 mm in width.

*Stem shape*.—Oval.

*Stem color*.—A blend of 137D and 138C.

*Stem surface*.—Hairless, satiny but glaucous.

Foliage description:

*Leaf shape*.—Compound.

*Leaf division*.—Ternate.

*Leaf internode*.—Foliage begins 15 cm from base, an average of 10 cm on main stem and an average of 8 cm on secondary branches.

*Leaf size*.—An average of 5 cm in length and 6.3 cm in width.

*Leaf quantity*.—About 17 per stem.

*Leaflet shape*.—Oblanceolate.

*Leaflet base*.—Cuneate.

*Leaflet apex*.—Acute.

*Leaflet venation*.—Pinnate pattern, not conspicuous, midrib on lower surface conspicuous, upper and lower surface 145B in color.

*Leaflet margins*.—Entire.

*Leaf attachment*.—Petiolate.

*Leaf arrangement*.—Alternate.

*Leaflet surface*.—Glabrous and slightly glaucous on upper and lower surface.

*Leaflet color*.—Newly expanded; upper and lower surface a blend of 138A and 137C, mature; upper and lower surface 137B.

*Leaflet size*.—An average of 5 cm in length and 2.3 cm in width.

*Petioles*.—Average of 5 mm in length and 1.9 mm in width, clasping to stem, 144B in color, surface is glabrous and satiny.

*Stipules*.—On basal 1 to 2 nodes prior to leaves; single, oblanceolate in shape, an average of 2.5 cm in length and 1 cm in width, clasping to stem, acute apex, 138A and 138C at base in color, on leaf nodes and base of peduncle; 2, oblanceolate in shape, base is truncate to stem, apex is acute, average of 8 mm in length and 4.5 mm in width on mature leaves, 137A in color on upper and lower and surface and 138C at the base, surface is glabrous and slightly glaucous on upper and lower surface.

Flower description:

*Inflorescence type*.—Terminal racemes of zygomorphic flowers on main and secondary branches, blooms from the base to the apex.

*Inflorescence size*.—Average of 42 cm in length and 5 cm in width in mid section.

*Lastingness of inflorescence*.—About 3 weeks.

*Flower size*.—About 2.6 cm in depth and about 1.5 cm in diameter.

*Flower fragrance*.—Faint.

*Flower number per inflorescence*.—An average of 40.

*Peduncle*.—Oval to hexagonal in shape, up to 50 cm in length and an average of 4 mm in width, a blend of 137D and 138C in color lightly suffused with N92D, surface is glabrous, satiny and slightly glaucous, flower internode length averages from whorls to about 3 mm.

*Pedicel*.—About 7.5 mm cm in length, about 1 mm in width, oval in shape, a blend of 137D and 138C in color lightly suffused with N92D, glabrous and satiny surface.

*Flower buds*.—Kidney-shaped, about 1 cm in length and 0.5 cm in width, color of petal portion is N92D, calyx portion same as open flowers but suffused more with N92D.

*Flower type*.—Papilionaceous, held at about a 30° angle to the lateral branch.

*Calyx*.—Campanulate, about 8.5 mm in length and 5 mm in diameter, surface is glabrous and satiny, 137D and 138C in color lightly suffused with N92D, persistent.

*Sepals*.—4, fused with the exception of the apex of each, free portion is triangular in shape 3 or 4 mm in width and 4 mm in depth with an acute apex, except 4 mm wide section which has a notched apex, a blend of 137D and 138C in color and lightly suffused with N92D with areas completely N92D at the base of each free portion.

*Corolla features*.—Papilionaceous (4 segments) with a keel, a banner and 2 lateral wings, lateral wings; oval in shape, an average of 1.9 cm in length and 9 mm in width, color on outer surface and the inner surface is N88A with very basal portion NN155A and lightly suffused with 150A, rounded apex, oblique base, keel; only partially visible, comprised of 2 segments surrounding reproductive organs, obelliptic to obovate in shape with rounded apex and oblique base, 1.7 cm in length and 9.5 mm in width, upper surface and lower surface are N88A in color (NN155A at very base), banner; orbicular in shape, held flat to slightly backswept about 2.1 cm in length and 2.4 cm in width, upper and lower surface is a blend of N88A and N89B with the basal portion 145B to 145C, apex is rounded with a single notch, surface is glabrous on all sections.

*Receptacle*.—Disk-shaped, gelatinous, 143A in color, about 2 mm in diameter and 1.4 mm in depth.

Reproductive organs:

*Gynoecium*.—1 Pistil, about 2.4 cm in length, 1 mm in width; style is 144B in color and 14 mm in length; stigma minute, too small to read color, ovary is superior with a stipe, 143A in color, 5 mm in length and 1.2 mm in width; stipe is 144B in color, 3.5 mm in length and 1 mm in width.

*Androcoecium*.—10 stamens, not united, 2.1 cm in length and 1 mm in width; filament is 2 cm in length, 1 mm in width and 145D in color; anther is dorsifixed, 1 mm in length and 0.8 mm in width and 21A in color, pollen is abundant and 21A in color.

*Fruit*.—An inflated pod, technically a legume, when open pollinated; about 6 produced per inflorescence with open-pollinated, oblong in shape, average of 3.5 cm in length and 1.8 cm in width; each with a beak about 1.2 cm in length, color of inner and outer surface when young is a blend of 144A and 144B, color of outer surface when mature is a color between 201A and 202A, color of inner surface 197A to 199A, walls 1.5 mm and hard at maturity, seed; average of 11, 165B in color, oval with the hilum side more or less straight, seed compressed to flattish, 4 mm in length, 3 mm in width and 2 mm in thickness.

It is claimed:

1. A new and distinct cultivar of *Baptisia* plant named 'Royal Purple' as herein illustrated and described.

* * * * *